United States Patent
Seaman et al.

(10) Patent No.: US 9,151,683 B2
(45) Date of Patent: Oct. 6, 2015

(54) ANALYZING LOAD BEARING MEMBERS

(71) Applicant: STRAINSONICS LIMITED, Rotherham, South Yorkshire (GB)

(72) Inventors: Peter Seaman, Rotherham (GB); Philip Brian Harper, Sheffield (GB)

(73) Assignee: Strainsonics Limited, Rotherham, South Yorkshire (GB)

(*) Notice: Subject to any disclaimer, the term of this patent is extended or adjusted under 35 U.S.C. 154(b) by 0 days.

(21) Appl. No.: 14/344,885

(22) PCT Filed: Sep. 17, 2012

(86) PCT No.: PCT/GB2012/052288
§ 371 (c)(1),
(2) Date: Mar. 13, 2014

(87) PCT Pub. No.: WO2013/038208
PCT Pub. Date: Mar. 21, 2013

(65) Prior Publication Data
US 2014/0338463 A1 Nov. 20, 2014

(30) Foreign Application Priority Data

Sep. 15, 2011 (GB) .................. 1116014.0
Aug. 1, 2012 (GB) .................. 1213679.2

(51) Int. Cl.
*G01N 29/04* (2006.01)
*G01L 1/10* (2006.01)
*G01N 3/08* (2006.01)

(52) U.S. Cl.
CPC ... *G01L 1/10* (2013.01); *G01N 3/08* (2013.01)

(58) Field of Classification Search
CPC .......... G01L 1/10; G01L 1/2225; G01H 1/04; G01N 3/08
USPC ............................. 73/801, 785, 760
See application file for complete search history.

(56) References Cited

U.S. PATENT DOCUMENTS

| | | | |
|---|---|---|---|
| 3,587,296 A | 6/1971 | Kammer | |
| 3,754,610 A * | 8/1973 | Paelian et al. | 177/211 |
| 3,918,294 A * | 11/1975 | Makino et al. | 73/581 |
| 4,486,136 A * | 12/1984 | Howard | 414/21 |
| 5,195,381 A * | 3/1993 | Keibler | 73/862.05 |
| 5,205,176 A | 4/1993 | Kibblewhite | |
| 5,220,839 A * | 6/1993 | Kibblewhite | 73/761 |
| 2007/0151390 A1 * | 7/2007 | Blumenkranz et al. | 74/490.06 |
| 2007/0231078 A1 * | 10/2007 | Couch | 405/223.1 |
| 2010/0018938 A1 * | 1/2010 | Waisanen | 212/274 |

FOREIGN PATENT DOCUMENTS

| | | |
|---|---|---|
| EP | 1933121 A2 | 6/2008 |
| GB | 2462719 A | 2/2010 |
| JP | 1182727 A | 7/1989 |
| JP | 2001-304992 A | 10/2001 |

* cited by examiner

*Primary Examiner* — Max Noori
(74) *Attorney, Agent, or Firm* — patenttm.us

(57) ABSTRACT

A method of analyzing a load bearing member (12), comprises providing the load bearing member in a condition in which it is secured to a formation with a securing assembly (14). A predetermined load is applied to the load bearing member, thereby stressing the securing assembly. A signal is transmitted through a component (24, 108) of the securing assembly transverse to the direction at which the load is applied, and a measurement is taken of an effect on the signal to determine the aforesaid load.

18 Claims, 21 Drawing Sheets

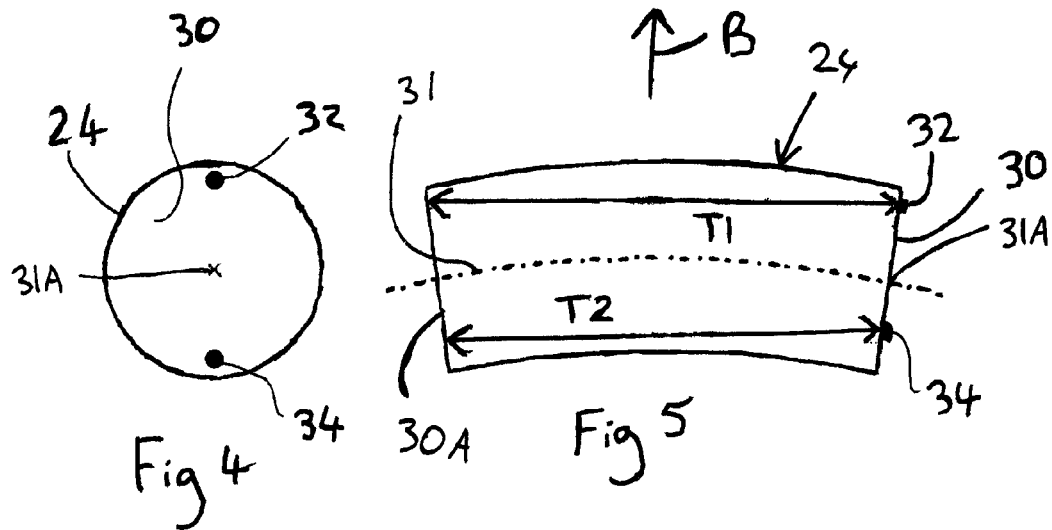
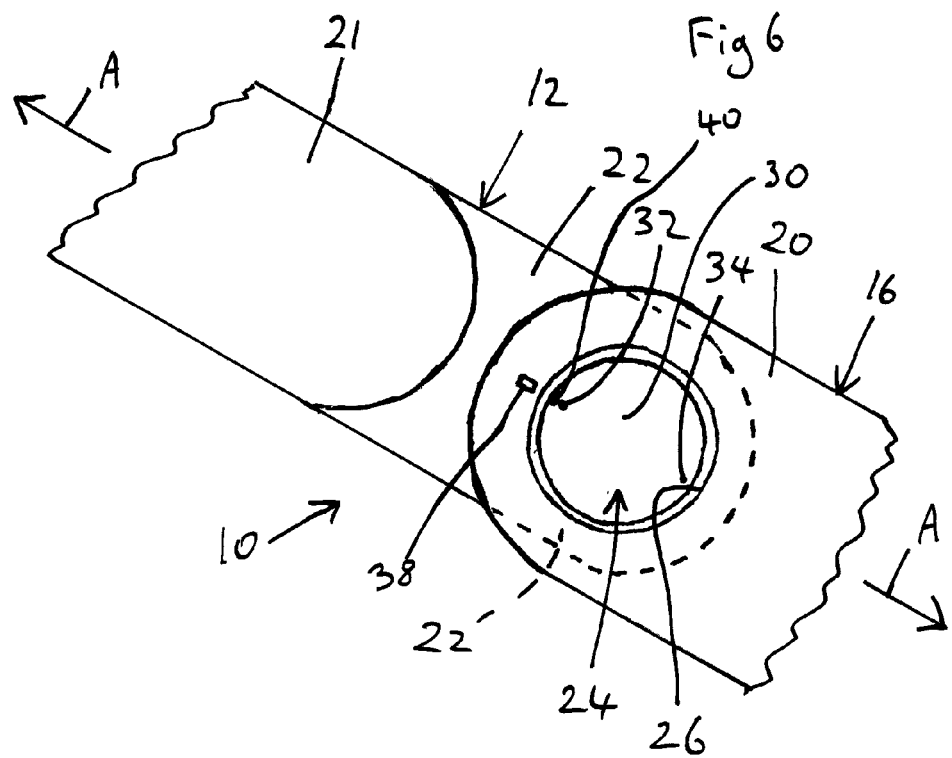

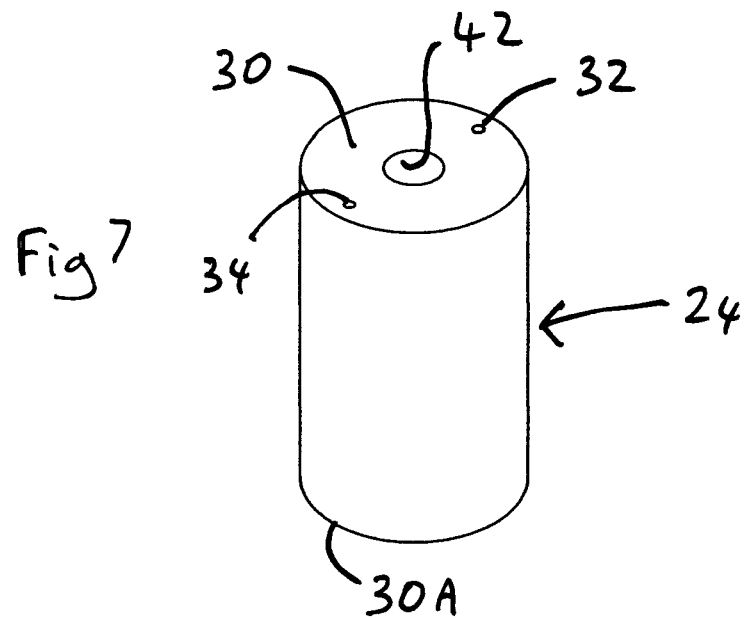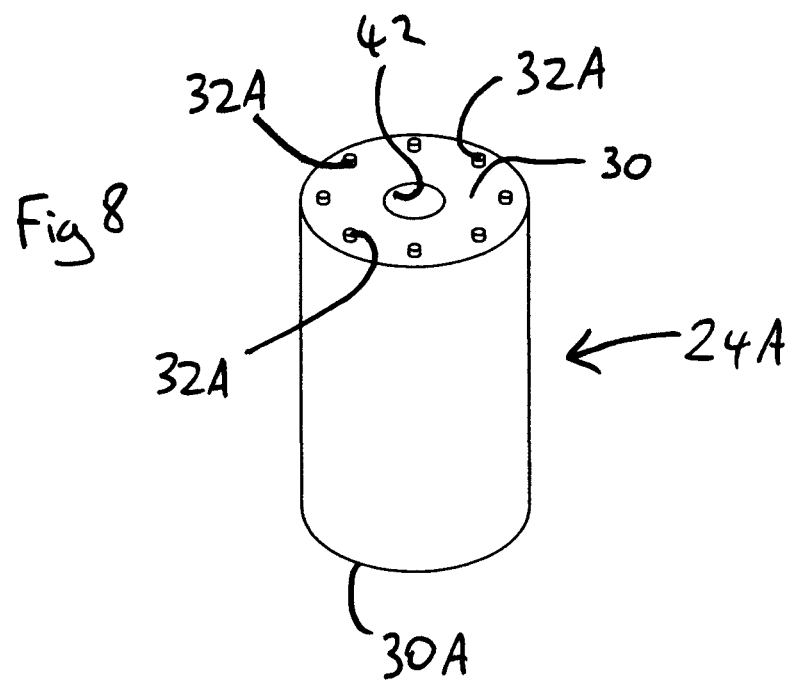

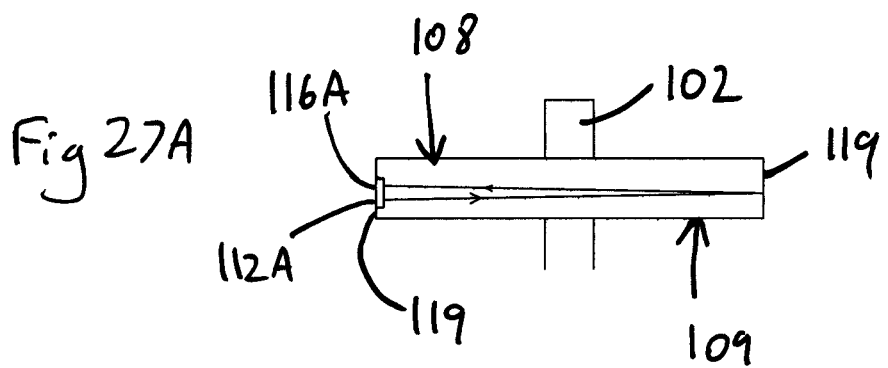
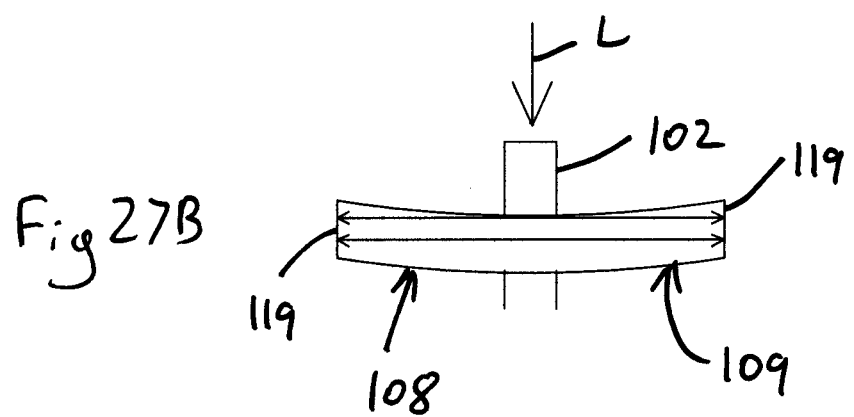
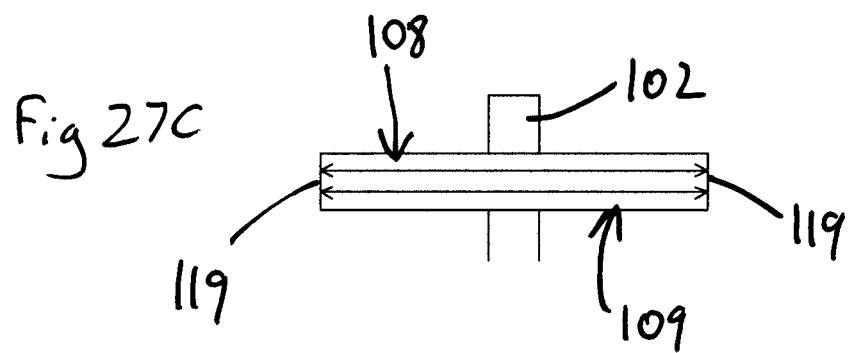

ANALYZING LOAD BEARING MEMBERS

This invention relates to methods of analysing load bearing members. More particularly, but not exclusively, this invention relates to methods of determining tension or compression in load bearing members secured by securing assemblies. This invention also relates to methods of analysing components of securing assemblies members. More particularly, but not exclusively, this invention relates to methods of determining tension or compression in components of securing assemblies.

The determination of the tension in a structural member is described in GB2462719A.

According to one aspect of this invention, there is provided a method of analysing a load bearing member, comprising providing the load bearing member in a condition in which it is secured to a formation with a securing assembly, applying a load to the load bearing member, thereby stressing the securing assembly, transmitting a signal through a component of the securing assembly transverse to the direction at which the load is applied, and taking a measurement of an effect on the signal to determine the aforesaid load.

According to another aspect of this invention, there is provided a method of analysing a component of a securing assembly, comprising providing a load bearing member in a condition in which it is secured to a formation with the securing assembly, applying a predetermined first load to the load bearing member, thereby applying a second load to the securing assembly, transmitting a signal through a component of the securing assembly transverse to the direction at which the first load is applied, and taking a measurement of an effect on the signal to determine the aforesaid second load.

According to another aspect of this invention, there is provided a component of a securing assembly, said securing assembly being for use in securing a load bearing member, wherein the component of the securing assembly comprises a face and first and second signal emitters.

The signal may be transmitted through a component of the securing assembly substantially orthogonally to the direction at which the load is applied. A plurality of signals may be transmitted through the aforesaid component of the securing assembly. A measurement may be taken of an effect on each signal to determine the aforesaid load. In one embodiment, no more than two signals may be transmitted through the aforesaid component of the securing assembly.

In the embodiments described herein, the load bearing member is analysed indirectly by measurements taken on the aforesaid component of the securing assembly. In these embodiments, the analysis of the aforesaid component of the securing assembly may be an indirect measurement of the load on the load bearing member.

The method may comprise emitting the signal along a dimension of the aforesaid component of the securing assembly.

The aforesaid component of the securing assembly may comprise a securing member. In a first embodiment, the securing member may comprise a pin. In the first embodiment, the dimension may extend lengthwise of the aforesaid component of the securing assembly. In a second embodiment, the securing member may comprise a load spreading member, which may comprise a washer or a load bearing plate. In the second embodiment, the dimension may extend across the aforesaid component of the securing assembly.

In the second embodiment, the aforesaid component of the securing assembly may define an aperture, through which the load bearing member can extend.

The load applied to the load bearing member may be a predetermined load. The load applied to the load bearing member may be a tension load or a compression load. The load applied to the load bearing member may be applied longitudinally of the load bearing member. The load applied to the load bearing member may be applied in the plane of the aforesaid component of the securing assembly.

The signal may comprise a sound wave, or a plurality of sound waves. The signal may be an ultrasonic wave, or a plurality of ultrasonic waves. The effect on the signal measured may be the time for the signal to transmit through the aforesaid component of the securing assembly, the frequency or frequency range of the signal and/or the amplitude or amplitude range.

The aforesaid component of the securing assembly may extend transverse to the load bearing member. The stressing of the aforesaid component of the securing assembly may cause the aforesaid component of the securing assembly to deform, for example by bending. The method may include recording the measurement on a recording medium.

The step of emitting the signal may comprise emitting the signal from an emission point on an emission face of the aforesaid component of the securing assembly to a further face, or to a further region of the same face, of the aforesaid component of the securing assembly. The further face may be opposite the emission face. The further region of the same face may be opposite the emission point.

Alternatively, the step of emitting the signal may comprise emitting the signal from an emission face of the aforesaid component of the securing assembly to a discontinuity in the aforesaid component of the securing assembly. The step of emitting the signal may comprise emitting the signal at an emission point, which may be at an edge region of the aforesaid component of the securing assembly.

The step of emitting the signal may comprise emitting the signal from an emission device arranged at the, or each, emission point.

In one embodiment, the, or each, face may be an edge face. In another embodiment, the, or each, face may be an end face.

The method may comprise taking a plurality of measurements from a plurality of emission points on the face of the aforesaid component of the securing assembly. The method may comprise taking a plurality of measurements from two emission points on the face of the aforesaid component of the securing assembly.

The aforesaid component of the securing assembly may have a plurality of the emission points. The aforesaid component of the securing assembly may have two of the emission points.

Each emission point may have a respective signal emitter provided thereon.

Each emission point may comprise a marked region on the face. The signal emitters may be provided on the marked regions.

In the first embodiment, the aforesaid component of the securing assembly may have an end face, and the emission point may be on the end face. The emission point may be aligned with the load applied to the load bearing member.

In a first embodiment, the aforesaid component of the securing assembly may have an end face. The method may comprise taking a plurality of measurements at a plurality of emission points around the end face. The plurality of emission points may be spaced from a substantially central point of the end face. The plurality of emission points may be provided radially outwardly from the substantially central point of the end face. The plurality of emission points may extend circumferentially around the substantially central point of the end face. The plurality of emission points may be substantially equally spaced from a substantially central point of the end face. The plurality of emission points may be substantially equally spaced from adjacent emission points.

In the second embodiment, the aforesaid component of the securing assembly may comprise an edge face, and the plurality of emission points may be provided on the edge face. Alternatively, the aforesaid component of the securing assembly may comprise a plurality of edge faces, and the plurality of emission points may be provided on adjacent edge faces.

The method may comprise emitting first and second signals along the dimension of the aforesaid component of the securing assembly, said first and second signals being transverse to the direction of application of the load applied to the load bearing member. The two emission points are desirably aligned with direction of the load applied to the load bearing member, said alignment being such that an imaginary line extending between the two emission points extends parallel to the direction of the load applied to the load bearing member.

The method may include taking first and second measurements of respective effects on the first and second signals. The method may include recording the first and second measurements on a recording medium. In one embodiment, the method may comprise taking three or more of the measurements at respective emission points around the end face. Where three or more such measurements are taken, the alignment of any of the emission points with the load applied to the load bearing member is not necessary.

The signals may be emitted and/or received by an electronic emission/receiving device, for example an ultrasonic emitter/receiver. One of the electronic emitting/receiving devices may be mounted at the, or each, emission point.

The step of emitting the first and second signals may comprise emitting the first and second signals from each emission point on the emission face to the further face of the aforesaid component of the securing assembly, or to a further region of the same face of the aforesaid component of the securing assembly, to be reflected from the further face, or from the further region, to a receiving point. The signal may be reflected from a plurality of faces or regions before being directed to the emission point. The receiving point may be the emission point.

In the first embodiment, the step of emitting the first and second signals may comprise emitting the first and second signals from one end face of the aforesaid component of the securing assembly to be reflected back from the opposite end face, or from one or both end faces to a discontinuity in the aforesaid component of the securing assembly.

The step of emitting the first and second signals may comprise emitting the first and second signals at the respective first and second emission points. The first and second emission points may be on the end face of the aforesaid component of the securing assembly. The first and second emission points may be aligned with the load applied to the load bearing member.

In the second embodiment, the step of emitting the first and second signals may comprise emitting the first and second signals from emission face of the aforesaid component of the securing assembly to be reflected back from the opposite further face, or from the further region of the same face, or from one or both faces or regions to a discontinuity in the aforesaid component of the securing assembly.

The step of emitting the first and second signals may comprise emitting the first and second signals at the respective first and second emission points.

Alternatively, the method may comprise emitting respective signals from opposite faces, or from opposite regions of the same face, of the aforesaid component of the securing assembly, wherein the signals emitted from a first of the faces are detected by at least one electronic emission/receiving device at an opposite second of the faces, or at the opposite region of the same face, and/or the signals so emitted may be detected by the electronic emitting/receiving device.

The aforesaid component of the securing assembly may have a centre line extending through the end face at a centre point, the centre line extending transverse to the load applied to the load bearing member. The first and second emission points may be spaced from the centre point. In one embodiment, the first and second emission points may be substantially equidistant from the centre point. The first and second emission points may be provided opposite each other with the centre point therebetween.

The step of determining the load applied to the load bearing member may comprise determining the difference between the first and second measurements. In at least one of the embodiments described herein, this provides the advantage that the aforesaid difference in measurements is independent of changes in the dimension, speed of sound or other material properties due to changes in temperature.

The, or each, measurement may be taken during elastic load deformation of the aforesaid component of the securing assembly. In the second embodiment, the aforesaid component of the securing assembly may define a recess to facilitate, or allow the elastic deformation thereof.

The first signal may be emitted through a region of the aforesaid component of the securing assembly that is in tension during said stressing of the component. The second signal may be emitted through a region of the aforesaid component of the securing assembly that is in compression during said stressing of the component.

The first signal may be emitted through a region of the aforesaid component of the securing assembly that is in tension during said deformation. The second signal may be emitted through a region of the aforesaid component of the securing assembly that is in compression during said deformation.

The method may comprise marking the aforesaid component of the securing assembly to align the aforesaid component of the securing assembly appropriately relative to the formation and/or the load bearing member when the aforesaid component of the securing assembly is installed therein. The aforesaid component of the securing assembly may be marked by stamping, engraving, embossing, chemical marking, laser marking, laser oblation or any other suitable method. Alternatively, the aforesaid component of the securing assembly may have an electronic chip mounted therein to identify the component. The chip may have an identification means, such as a serial number or the like.

Alternatively, or in addition, the method may comprise marking the load bearing member or on the formation. The marking may be on the load bearing member or on the formation may be provided to align the aforesaid component of the securing assembly appropriately relative to the formation and/or the load bearing member when the aforesaid component of the securing assembly is installed therein. The corresponding marking may be provided on the aforesaid component of the securing assembly for alignment with the first mentioned marking.

A recording of the, or each, measurement may comprise recording the, or each, measurement or recording a parameter or a derived parameter, of the measurement, on an electronic memory device in the electronic emission/receiving device, or on a database of a data processing arrangement. The database may include further details of the load bearing member and/or of the aforesaid component of the securing assembly. Alternatively, if desired, a step of recording the, or each, measurement may comprise writing the, or each, measurement on a suitable record sheet.

The step of taking the, or each, measurement may comprise emitting from a signal emission device, such as the electronic emission/receiving device, a signal to be emitted along the aforesaid component of the securing assembly. The signal emitted along the aforesaid component of the securing assembly may be transverse to the direction of the load applied to the load bearing member.

The signal may be reflected from an opposite face, or an opposite region of the same face, of the aforesaid component of the securing assembly, or from a discontinuity in the aforesaid component of the securing assembly. Alternatively, the signal may be emitted from a third electronic emission/receiving device at the opposite end of the aforesaid component of the securing assembly.

The step of taking the, or each, measurement may comprise measuring the, or each, period of time for the, or each, signal to return to the, or each, measurement point on the aforesaid component of the securing assembly, known as the time of flight. Alternatively, the step of taking the, or each, measurement may comprise measuring the amplitude or frequency variation of the signal, or a combination of two or more of the time of flight, the amplitude and the frequency.

An example of a suitable electronic emission/receiving device is sold by NDT Solutions. An oscilloscope may be required to process the results of the measurements. A suitable oscilloscope is sold by Le Croy Limited.

The recording of the, or each, measurement may include recording one or more items of information from the following: the length of the, or each, dimension; the identity of the material of the aforesaid component of the securing assembly; the cross sectional area of the aforesaid component of the securing assembly; the maximum force the aforesaid component of the securing assembly is designed to accommodate; the serial number of an electronic chip embedded in the aforesaid component of the securing assembly.

The recording of the information may comprise recording one or more further items of information selected from the following: the date of manufacture of the aforesaid component of the securing assembly; the type of aforesaid component of the securing assembly; the type of designation of the equipment used; the batch number of the aforesaid component of the securing assembly; the serial number of the aforesaid component of the securing assembly; the unique I.D. of the aforesaid component of the securing assembly; the date of calibration of the aforesaid component of the securing assembly.

Prior to taking the, or each, measurement, the method may comprise taking calibrating measurements.

The step of taking the calibrating measurements may comprise arranging the aforesaid component of the securing assembly, or a substantially identical component of the securing assembly, in a rig, and emitting a signal, or a plurality of signals, along the dimension of the aforesaid component of the securing assembly.

The step of taking the calibrating measurements may comprise applying a force transverse to the dimension of the aforesaid component of the securing assembly along which the signal is emitted, and emitting the, or each, signal along the dimension while the force is applied.

The step of taking the calibrating measurements may comprise applying in sequence a plurality of forces transverse to the dimension and emitting a respective signal along the dimension while each of said forces applied to the aforesaid component of the securing assembly. The step of taking the calibrating measurements may comprise recording the measurements in correspondence with the respective forces applied to the aforesaid component of the securing assembly.

The step of taking the calibrating measurements may comprise applying in sequence a plurality of forces transverse to the dimension and emitting first and second signals along said dimension when each of said forces is applied. The step of taking the calibrating measurements may comprise recording the first and second measurements in correspondence with the respective forces applied to the aforesaid component of the securing assembly.

A calibrating graph may be plotted or force applied against either the calibrating measurement taken, or where only first and second calibrating measurements are taken, differences in the calibrating measurements.

The method may comprise comparing the measurements with the calibrating measurements to determine the force applied to the aforesaid component of the securing assembly and thereby determine the load applied to the load bearing member.

An embodiment of the invention will now be described by way of example only, with reference to the accompanying drawings, in which:

FIG. 4 shows an end view of a first embodiment of a component of the securing assembly;

FIG. 5 is a side view of the component of the securing assembly shown in FIG. 4, in which a bending force is applied thereto;

FIG. 6 is a view of an end face of the component of the securing assembly shown in FIG. 4, with the component of the securing assembly installed in a securing assembly;

FIG. 7 is a perspective view of an embodiment of a component of the securing assembly;

FIG. 8 is a perspective view of a further embodiment of a component of the securing assembly;

FIGS. 27A to 27C are sectional views showing the path of the signals emitted through the components of the securing assemblies shown in FIGS. 9 to 22;

Figure 1:
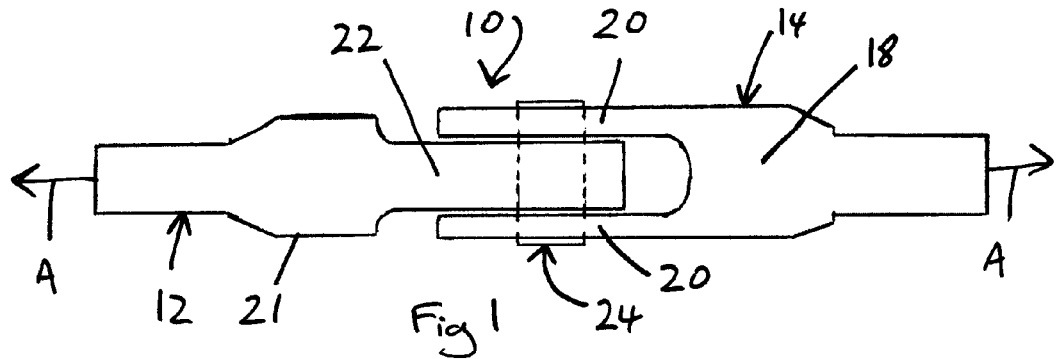
FIG. 1 shows a junction between an elongate load bearing member and a securing assembly of a first embodiment.

A junction 10 between an elongate load bearing member 12 and a securing assembly 14 in an architectural structure is shown in FIG. 1. In FIGS. 1 to 6, the elongate load bearing member 12 is in the form of a structural member, for example in the form of a tendon in a building structure. It will be appreciated by the skilled person that the structural member could be any suitable structural member, for use in constructing architectural structures, such as suspension bridges and the like.

The securing assembly 14 comprises a fork member 16 comprising a main part 18 and a pair of forks 20. The elongate load bearing member 12 comprises a main part 21 and an insertion portion 22, which is inserted between the forks 20. The securing assembly 14 further includes a component in the form of a securing member, comprising a pin 24.

The pin 24 is inserted through aligned apertures 26, 28 (see FIGS. 2 and 3) in the forks 20 and the insertion member 22 respectively. Thus, the elongate load bearing member 12 is secured to the securing assembly by the pin 24.

Figure 2:
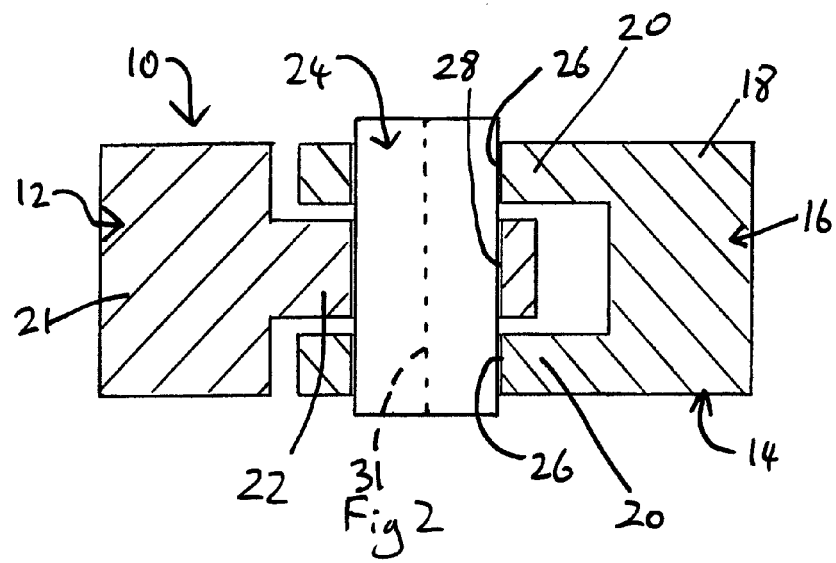
FIG. 2 shows a cross sectional diagrammatic view of the junction showing FIG. 1, with the components under no load.

FIG. 2 shows the joint 10 before any load is applied to the elongate load bearing member 12. As can be seen, the pin 24 in FIG. 2 is substantially straight. In the embodiment described herein, the load applied to the elongate load bearing member 12 is a tension load, but it will be appreciated that the invention could be used where the load is a compression load.

Figure 3:
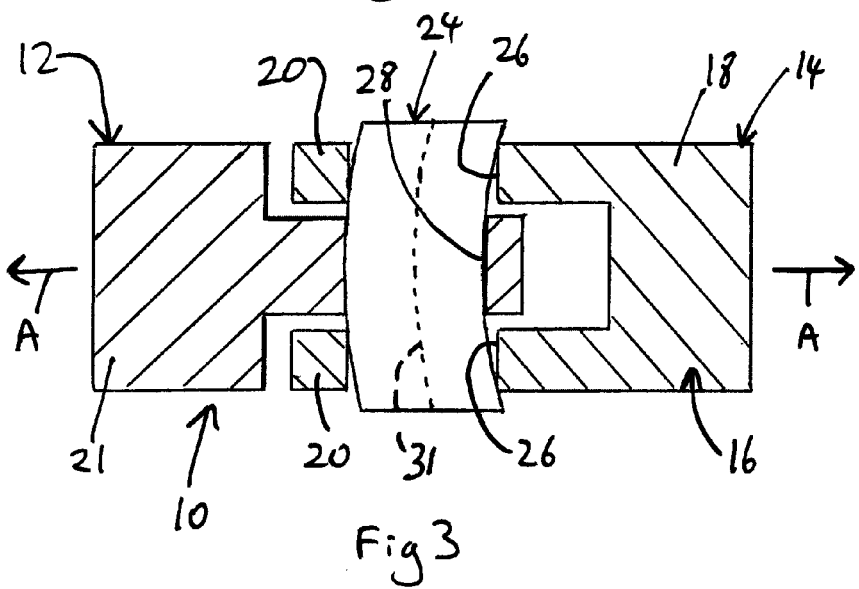
FIG. 3 shows a view similar to FIG. 2, but with the components under load.
Figure 9:
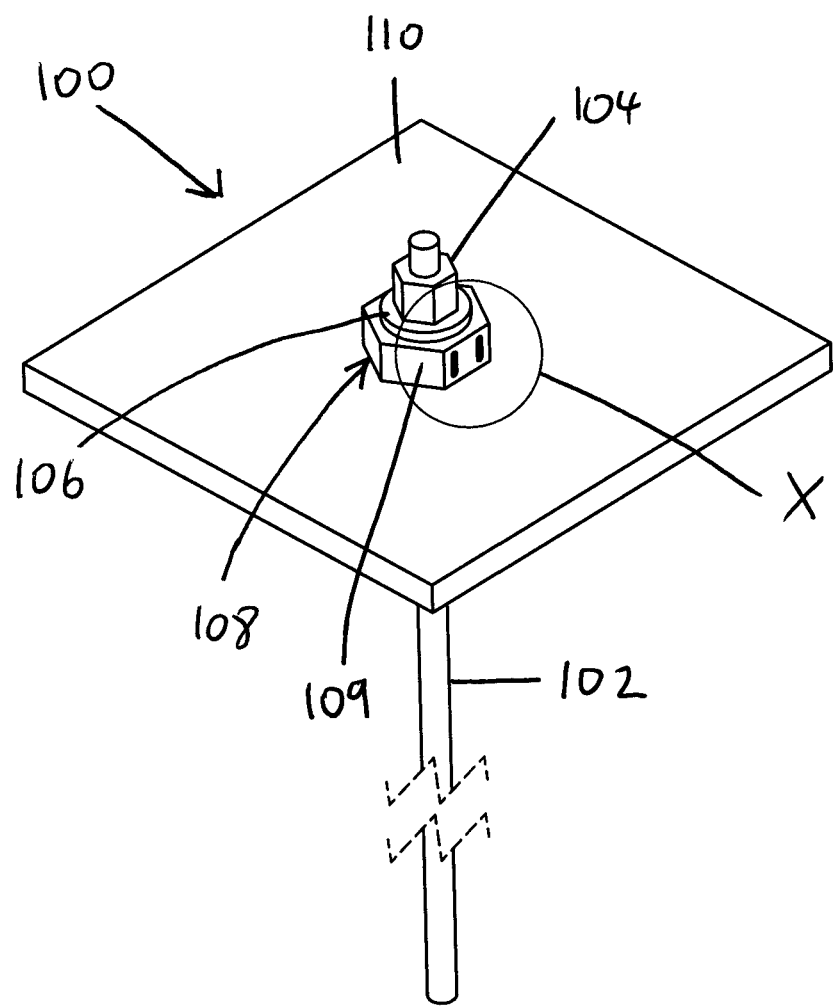
FIG. 9 is a perspective view showing a further embodiment of a securing assembly 100.
Figure 10:
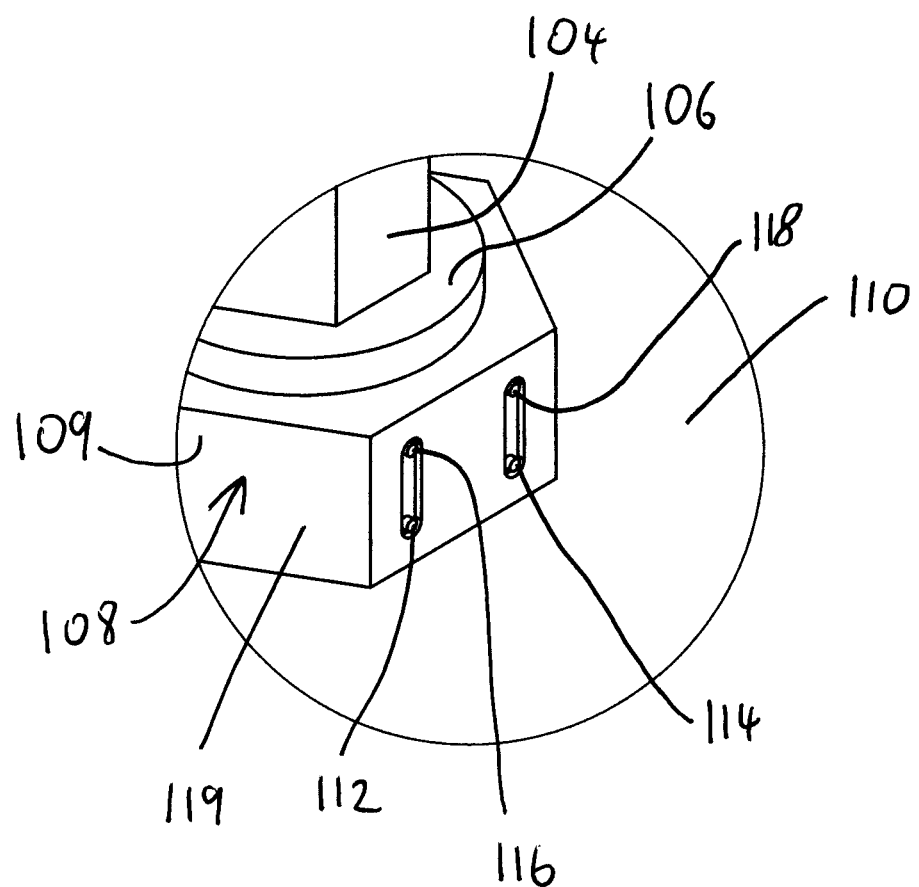
FIG. 10 is a view of the region marked X in FIG. 9.
Figure 11:
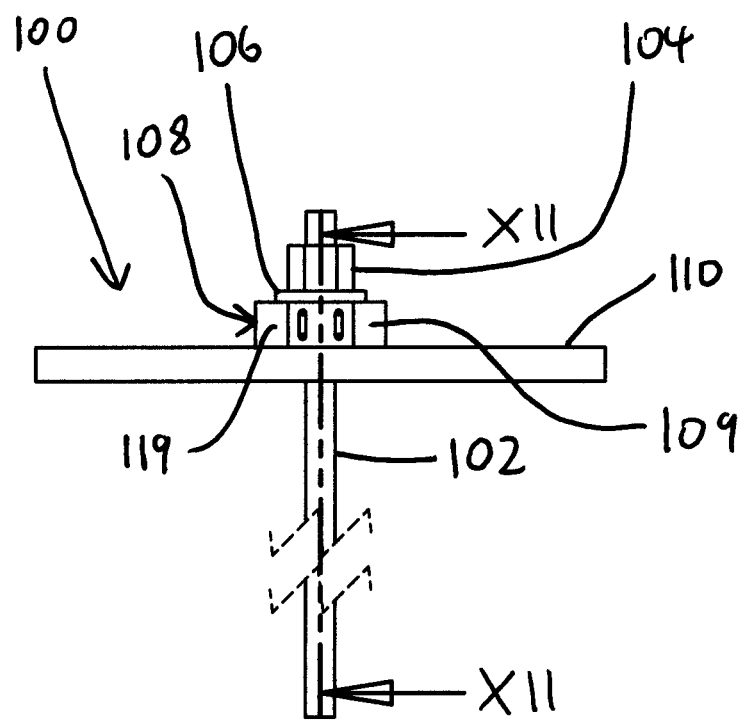
FIG. 11 is a side view of the securing assembly shown in FIG. 9.
Figure 12:
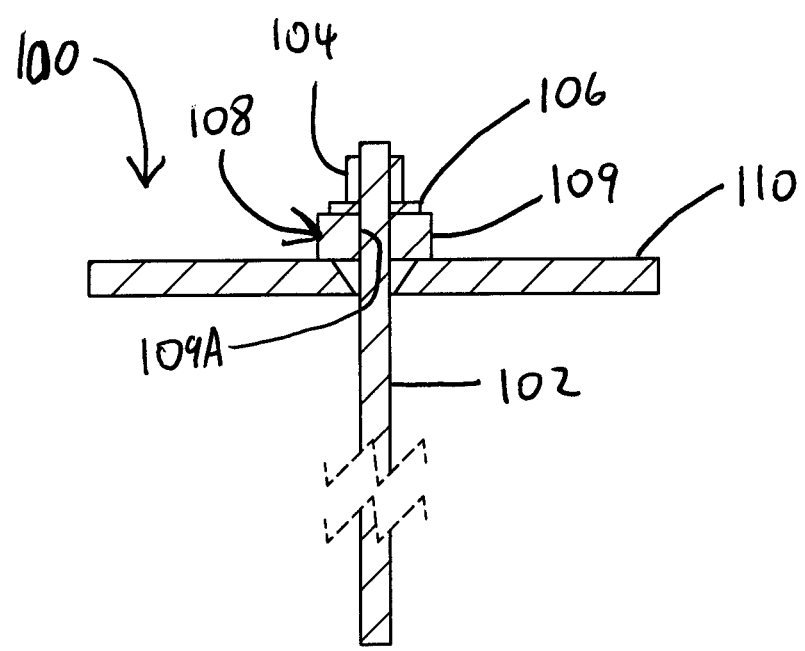
FIG. 12 is a view along the lines XII-XII in FIG. 11.

After the tension has been applied to the elongate load bearing member 12, as indicated by the arrows A in FIGS. 1 and 3, the insertion portion 22 pulls on the central region of the pin 24, and the forks 20 pull on the end regions of the pin 24. The result is that the pin 24 is stressed, and may deform by bending, as shown in FIG. 3. The above description of the joint 10 is a description of a standard joint between a securing assembly 14 and the elongate load bearing member 12 in many architectural structures, and other general engineering and would be understood by those skilled in the art.

In order to ensure that the elongate load bearing member 12 is at the correct tension after installation, and perhaps many years after installation, the tension needs to be checked. This can be done either by measuring the length of the elongate load bearing member 12 directly and comparing this measurement with calibrating measurements carried out prior to installation of the elongate load bearing member 12, for example as described in GB2462719A. Alternatively, as realised in the embodiments of the present invention described herein, a measurement can be made relating the stress applied to the pin 24 to the tension applied to the elongate load bearing member 12, as described below.

FIGS. 4 and 5 show respectively a first end face 30 of a pin 24 and a side view of the pin 24 which is bent by the tension applied to the elongate load bearing member 12.

The pin 24 has a centre line 31 extending longitudinally therethrough. The centre line 31 defines a centre point 31A on the first end face 30. First and second emission positions 32, 34 are provided at the edge region of the end face 30. The first and second emission positions 32, 34 are diametrically opposite each other, with the centre point 31A between them. The first and second emission points 32, 34 are substantially equidistant from the centre point 31A.

Respective electronic emission/receiving devices are mounted on the first end face 30 at each of the first and second emission points 32, 34. The pin 24 also has an opposite second end face 30A at its opposite end.

The emission/receiving device mounted at the first emission point 32 is connected to a suitable data monitor, such as an oscilloscope (not shown). A first signal in the form of a first sound wave, such as a first ultrasonic wave, is then emitted from the emission/receiving device mounted at the first emission point 32. The first sound wave is emitted through the pin 24 from the first emission point 32 on the first end face 30 and is reflected from the opposite second end face 30A, back to the first end face 30. The emission and reflection of the first sound wave is represented diagrammatically by the double headed arrow T1. The time of flight of the first sound wave, i.e. the time from its emission to its detection by the emission/receiving device is recorded.

A second signal, in the form of a second sound wave, such as a second ultrasonic wave, is emitted from the emission/receiving device mounted at the second emission point 34. The second sound wave is emitted through the pin 24 from the second emission point 34 and is reflected from the opposite second end face 30A back to the first end face 30. The second sound wave is represented diagrammatically by the double headed arrow T2. The time of flight of the second sound wave is recorded on detection by the electronic emission/receiving device.

The first measurement is taken at a region of the pin 24 that is in tension caused by the bending of the pin 24. The second measurement is taken at a region of the pin 24 that is in compression.

The times of flight of the first and second sound waves are dependent upon the temperature of the pin 24. The difference between the first and second measurements is, however, independent of the temperature and can therefore be used with this embodiment at any temperature of the pin 24.

The above description represents the method used for taking the first and second measurements. In order for the first and second measurements to be used in determining the tension in the elongate load bearing member 12, calibration measurements of the pin 24 or of a substantially identical pin are taken.

In order to perform the calibration measurements, a rig is set up in a testing facility in which an elongate load bearing member 12 is connected to a securing assembly 14, in the same way as shown in FIG. 1. A first predetermined tension is then applied to the elongate load bearing member 12. The applied tension is then recorded on a database or suitable record sheet. A first calibration measurement is then taken from the first emission point 32 using an emission/receiving device. An ultrasonic sound wave is emitted through the pin 24 from the first emission point 32, in the same way as described above.

A second calibration measurement is then taken from the second emission point 34, using the emission/receiving device mounted at the second emission point 34. Thus, first and second times of flight are measured. The difference between the first and second times of flight is then recorded in correspondence with the first applied predetermined tension.

The above calibration measurements are then repeated a plurality of times for a plurality of different predetermined tensions applied to the elongate load bearing member 12. Each time, the difference between the first and second measurements is recorded in correspondence with a respective tension applied to the elongate load bearing member 12. A graph can then be plotted of the applied tension against the difference between the respective first and second measurements.

In order to determine the tension in the elongate load bearing member 12 being checked on site, the difference between the first and second measurements is checked against the graph of the calibrated measurements.

The tension so determined provides the user with an indication of the structural health of the elongate load bearing member 12. The structural health of the elongate load bearing member 12 can be checked at regular intervals and, if necessary, appropriate adjustments can be made to the tension therein.

FIG. 6 shows a close-up side view of the junction 10 in which it can be seen that the first and second emission points 32, 34 are aligned with the tension applied to the elongate load bearing member 12, the tension being indicated by the arrow A. In order for the pin 24 to be inserted in the correct orientation in the apertures 26, 28 in the forks 20 and the insertion member 22, a first marking 38 is provided on the forks 20, and a second marking 40 is provided on the end face 30 of the pin 24. The first marking 38 is provided in line with the direction of the tension applied to the elongate load bearing member 12, as indicated by the arrow A.

On insertion of the pin 24 the second marking 40 is aligned with the first marking 38, thereby also aligning the first and second emission points 32, 34 with the direction of tension applied to the elongate load bearing member 12. It will be appreciated by those skilled in the art that the markings on the pin and fork could be anywhere around the circumference, not just aligned with the tension applied. There may be several markings on the pin 24 and on the forks 20 to facilitate alignment.

There is thus described a method of determining the tension in an elongate load bearing member 12 by analysing a securing pin 24 holding a elongate load bearing member 12 in place. The embodiment described and shown herein has the advantage that it allows the tension in the elongate load bearing member 12 to be examined by simple measurement of an effect on the, or each, sound wave emitted along the installed pin at two positions. The embodiment described herein has the advantage that it avoids the need for measurements to be taken at places on the elongate load bearing member 12 which may be difficult to access.

The method described herein has applications outside the field of construction, and could be used in for example, yachting, sailing, the shipping industry, on cranes, in loading environments, wind turbines, bolted anchoring connections, bolted joints or the like.

The inventors have devised a simple and ingenious method whereby the tension in an elongate load bearing member 12 can be easily determined by analysing the pin 24 which secures the elongate load bearing member 12 in place. The embodiment described herein is substantially independent of temperature.

Various modifications can be made without departing from the scope of the invention. For example, the pin 24 may have three measurement points on the first end face 30. The three measurement points may be spaced substantially equidistantly from one another about the circumferential edge region of the pin 24. The three measurement points may be spaced equidistantly from the centre point 31A. With the use of three measurement points aligning of the measurement points with the tension applied to the elongate load bearing member 12 may not be necessary. In another modification, it may be possible to calculate the tension in the elongate load bearing member 12 from the information obtained from the analysis of the pin 24.

It will be appreciated that, although the embodiment described herein relates to tension applied to the elongate load bearing member 12 in the plane of the pin 24, embodiments of the invention could also be used where the elongate load bearing member 12 is under compression in the plane of the elongate load bearing member 12. Other embodiments could also be used where the load is applied to the elongate load bearing member 12 out of the plane of the pin 24.

Embodiments of the invention may comprise taking a measurement of the load applied to the pin 24 itself. In these embodiments, the measurement is taken transverse to the load applied to the pin 24, in the same way as described above.

FIGS. 7 and 8 show further embodiments of the pin 24. FIG. 7 shows an embodiment which is similar to the pin 24 shown in FIGS. 4 and 5, in that the end face 30 possesses the first and second emission points 32, 34. The pin 24 shown in FIG. 7 differs from the pin 24 shown in FIG. 4, in that a central threaded recess to receive a bolt (not shown) used to secure in place a locking cover (not shown). The opposite end face 30A of the pin 24 shown in FIG. 7 also defines a central recess for receiving a similar bolt.

FIG. 8 shows a further pin 24A which is similar to the pin 24 shown in FIG. 7 in which the opposite faces 30, 30A define respective threaded recesses 42 for the same purpose as the recess 42 shown in FIG. 7. The pin 24A shown in FIG. 8 differs from the pin 24 shown in FIG. 7 in that a plurality of emission points 32A are provided circumferentially around the recess 42 defined in the end face 30. The emission points 32A are substantially equally spaced from each adjacent emission point 32A, and substantially equally spaced from the centre of the end face 30. The provision of the plurality of emission points 32A means that a plurality of readings or measurements can be taken thereby providing a more accurate assessment of the load on the pin and hence in the load-bearing member 12 (not shown) in FIG. 7 or 8.

The pin 24A is particularly suitable for use in situations where the position of the pin 24A rotates relative to the load bearing member, so that the direction of the load on the load bearing member rotates relative to the pin. This can occur, for example, in cranes, and an example is shown in FIGS. 28 to 31, and described below.

By emitting signals and taking measurements from each of the emission points 32A, the average of all the measurements can be calculated, thereby rendering the determination of the load independent of the position of the pin 24A relative to the load. Alternatively, the load vector can be calculated from the measurements taken from each emission point 32A, giving both angle and magnitude of load.

FIGS. 9 to 12 show a further embodiment of a securing assembly, generally designated 100, for securing an elongate load bearing member 102. The securing assembly 100 comprises a plurality of components, namely a nut 104, a washer 106, a measuring arrangement 108, and a load spreading plate 110. The nut 104 is threadably received on the threaded end of the elongate load bearing member 102, The elongate load bearing member 102 may be in the form, for example, of a rock bolt and may extend into the ground for the purposes of stabilising the ground. Alternatively, the elongate load bearing member 102 may extend to a component of a building, wherein the elongate load bearing member 102 acts as, for example, a structural tendon in the building, such as a bridge.

The measuring arrangement 108 comprises a load spreading main body 109 defining a central aperture 109A, through which the elongate load bearing member 102 extends. The measuring arrangement 108 further includes emission points comprising first and second signal emitting and receiving means, in the form of a first and second ultrasonic emitters 112, 114, and first and second ultrasonic receivers 116, 118. It will be appreciated that, although the ultrasonic emitters and receivers are shown separately, they could be the same device. The main body 109 shown in FIGS. 9 to 12 is of a hexagonal shape having six edge faces 119.

In use, when the nut 104 is tightened on to the threaded end of the elongate load bearing member 102 to tension it, the forces on the elongate load bearing member 102 and on the securing assembly 100 cause the main body 109 of the measuring arrangement 108 to be stressed. Thus, the main body 109 is deformed by bending such that the central region of the main body 109 is deformed towards the load spreading plate 110.

The extent of this deformation can be measured by emitting an ultrasonic signal from the first ultrasonic emitter 112. The signal is reflected off at least one of the faces 119 of the main body 109 and so that it is received by the first ultrasonic receiver 116. The time of flight of the signal is measured so that the distance travelled by the signal is thus determined using the measured time of flight and knowledge of the speed of sound in the material from which the main body 109 is made.

A further measurement can be taken by emitting a further ultrasonic signal from the second ultrasonic emitter 114, so that it is also reflected off at least one of the faces 119 of the main body 109 and received by the second ultrasonic receiver 118 to allow the distance travelled by the ultrasonic signal to be determined. The average of the two distances determined is recorded to provide an indication of the extent of deformation of the main body 109.

The measuring arrangement 108 can be calibrated in a Laboratory by applying known forces thereto and taking measurements as described above for each of those forces. Thus, when the above described measurements are taken with the measuring arrangement 108 in use in the field, an accurate determination can be made of the load thereon and, hence, the load on the elongate load bearing member 102.

Figure 13:
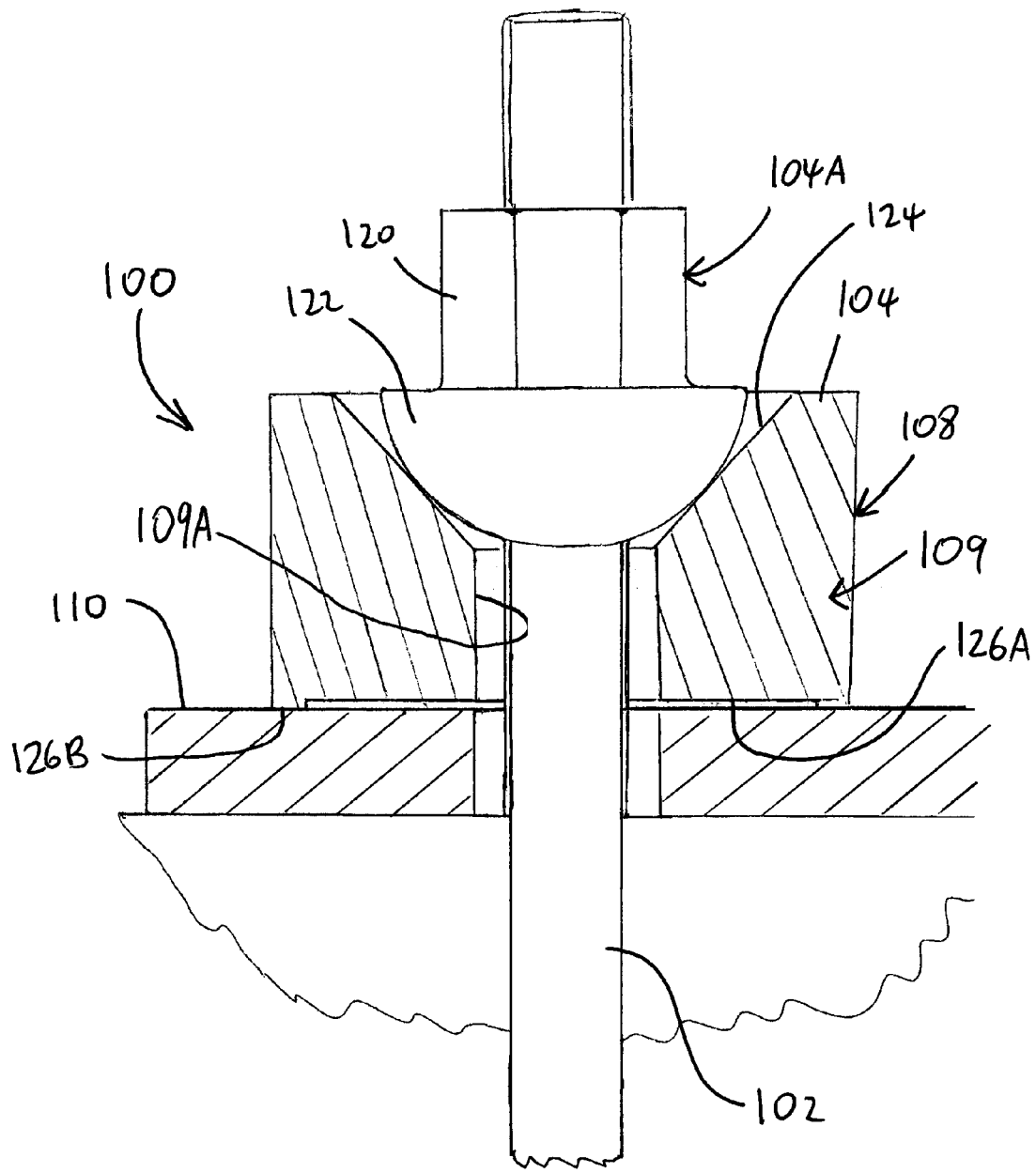
FIG. 13 is a sectional side view of a further embodiment of a securing assembly.
Figure 14:
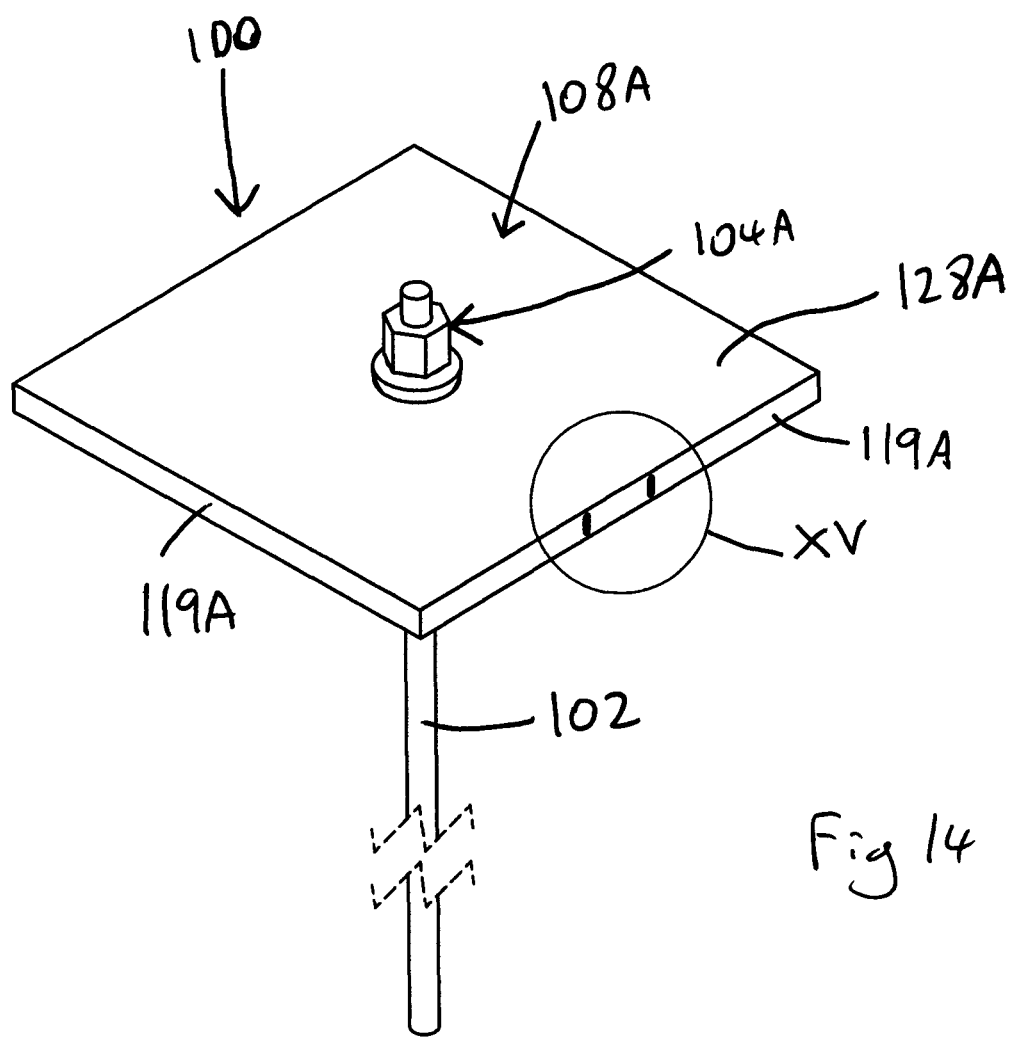
FIG. 14 is a perspective view of yet another embodiment of a securing assembly.
Figure 15:
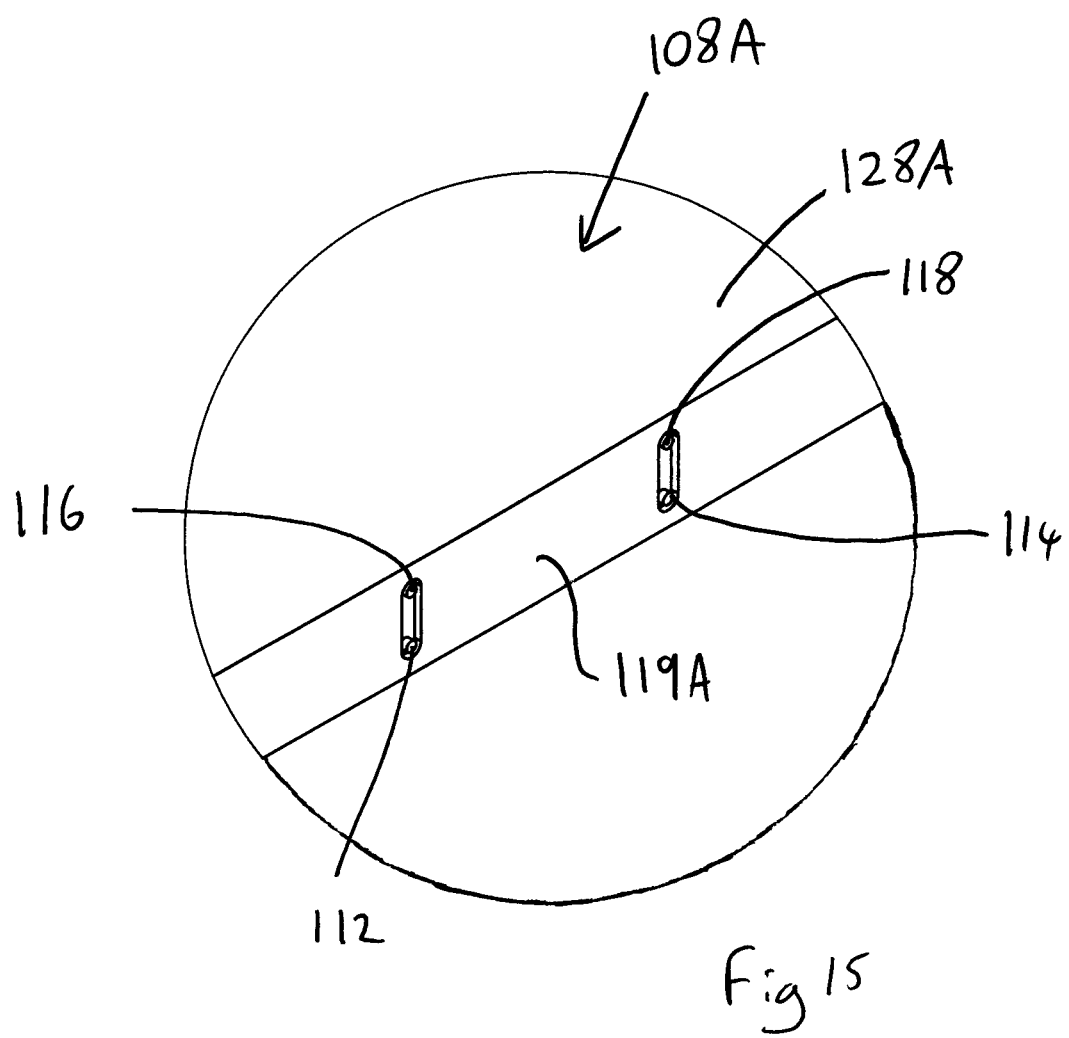
FIG. 15 is a close up view of the region marked XV in FIG. 14.
Figure 16:
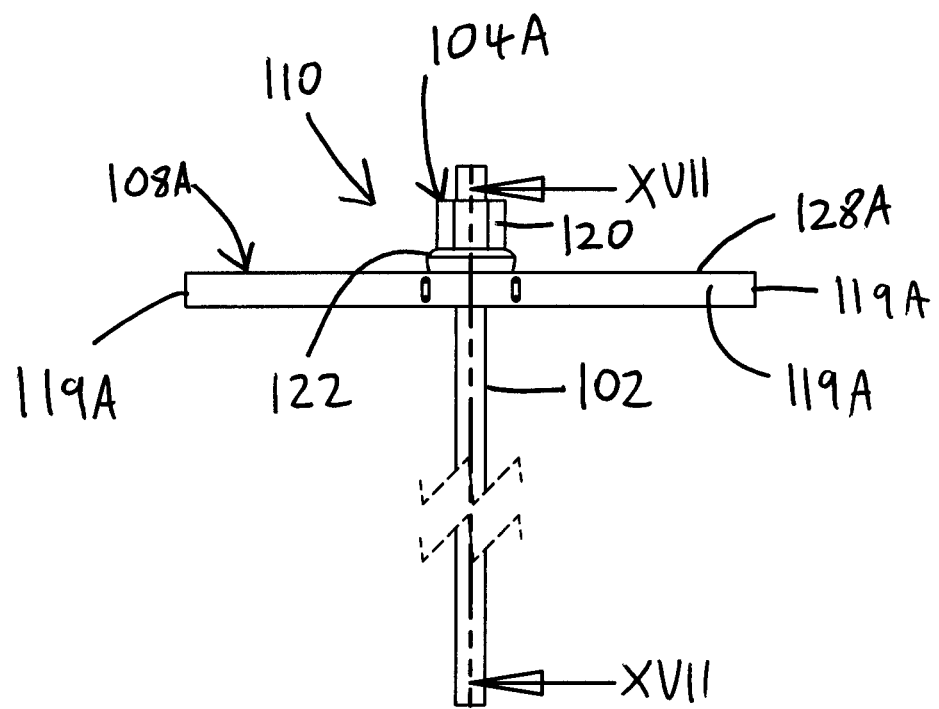
FIG. 16 is a side view of the embodiment shown in FIG. 14.
Figure 17:
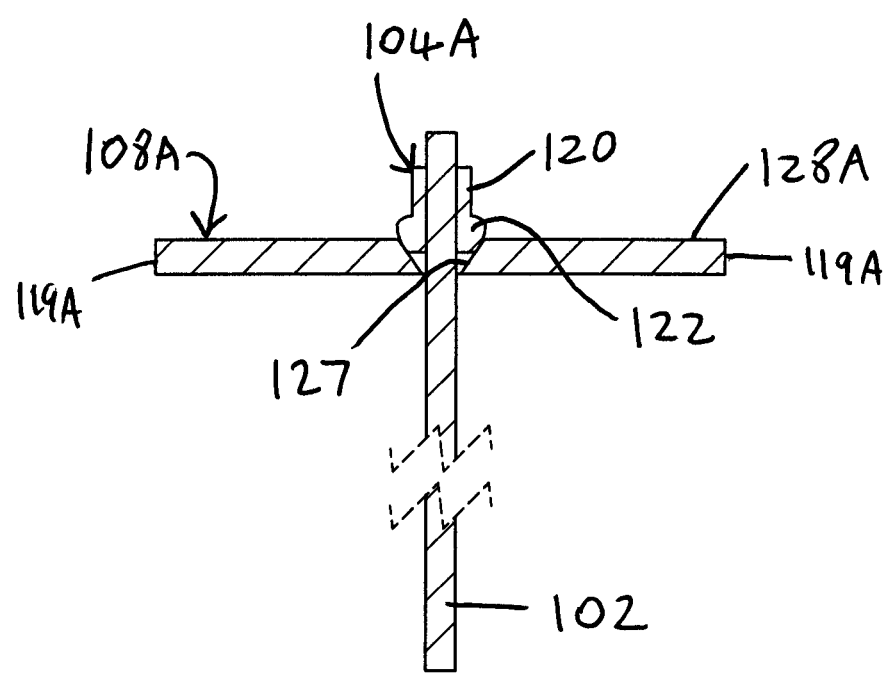
FIG. 17 is a sectional view along the lines XVII-XVII in FIG. 16.
Figure 18:
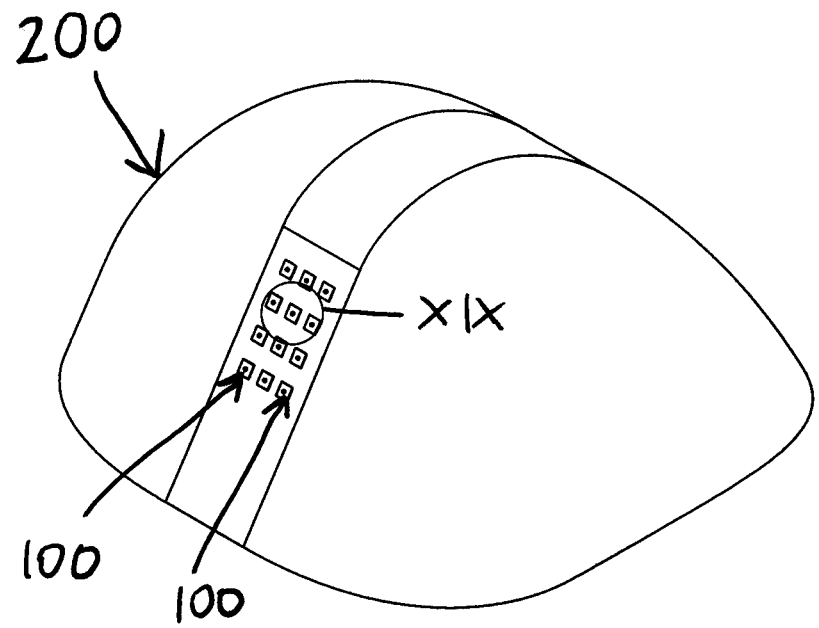
FIG. 18 shows a hill having a plurality of the securing assemblies shown in FIGS. 9 to 12 stabilising the hill.
Figure 19:
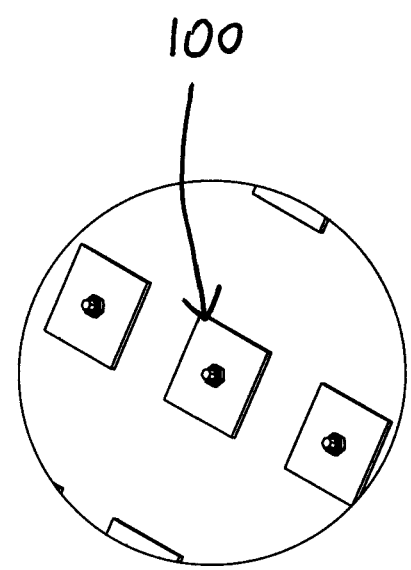
FIG. 19 is a close up view of the region marked XIX in FIG. 18.
Figure 20:
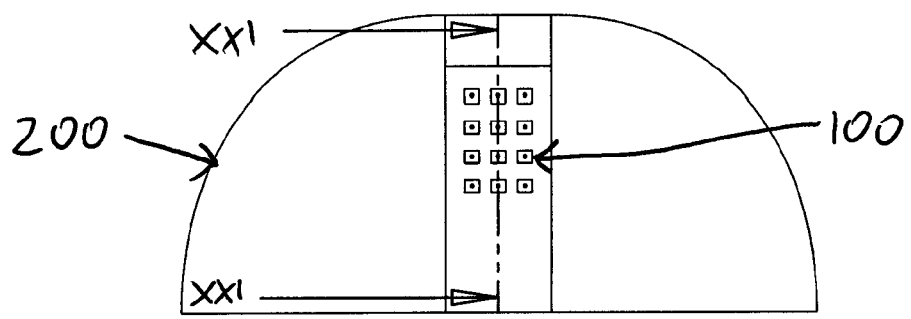
FIG. 20 is a front view of the hill shown in FIG. 18.

A modified version of the securing assembly 100 is shown in FIG. 13, in which the washer 106 has been omitted. A further difference is that the nut 104 is replaced by a nut 104A comprising a hexagonal shaped portion 120 and a dome shaped portion 122 on the hexagonal shaped portion 120. The main body 109 of the measuring arrangement 108 defines a frusto-conical recess 124 to receive the dome shaped portion therein. This has the advantage that the nut 104A can be secured to the threaded end of an elongate load bearing member 102 even when the elongate load bearing member 102 is not precisely at 90° to the load spreading plate 110.

Although not shown in FIG. 13, the measuring arrangement 108 also includes first and second ultrasonic signal emitting and receiving means.

FIG. 13 also shows a shallow recess 126A defined by the main body 109 of the measuring arrangement 108. FIG. 13 also shows a plate engaging face 126B, which engages the load spreading plate 110. The shallow recess 126A is pro-vided to allow the main body 109 to deform under load. This is explained in more detail below.

A further embodiment is shown in FIGS. 14 to 17, which differs from the embodiment shown in FIGS. 9 to 12, in that it does not include the washer 106. Also, the load spreading plate constitutes forms part of the measuring arrangement. In FIGS. 14 to 17, the measuring arrangement is generally designated 108A, and comprises the load spreading plate, designated 128A in FIGS. 14 to 17, which has a plurality of edge faces 119A. The measuring arrangement 108A also includes and the first and second ultrasonic signal emitting and receiving means 112, 114, 116 and 118.

In this embodiment, the securing assembly 100 further includes a nut 104A which is the same as the nut 104 shown in FIG. 13. The load spreading plate 128A defines a frusto-conical 127 recess to receive the dome shaped portion 122 of the nut 104A.

The measuring arrangement 108A shown in FIGS. 14 to 17 operates in generally the same way as the measuring arrangement 108 shown in FIGS. 9 to 12, in that the first and second ultrasonic signal emitting means 112, 114 emit the ultrasonic signals through the load spreading plate 128A of the measuring arrangement 108A to be reflected from the face 119A and received by the ultrasonic signal receiving means 116, 118. This provides a determination of the load on the load spreading plate 128A, and thereby the load on the elongate load bearing member 102.

FIGS. 18 to 21 show the securing assembly 100 of FIGS. 9 to 12 in use in stabilising the ground forming a hill 200.

Figure 21:
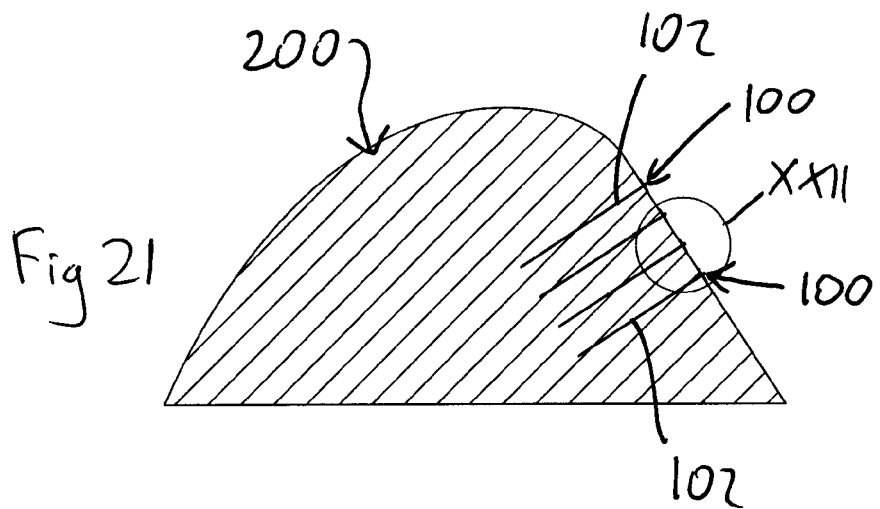
FIG. 21 is a sectional side view along the lines XXI-XXI in FIG. 20.
Figure 22:
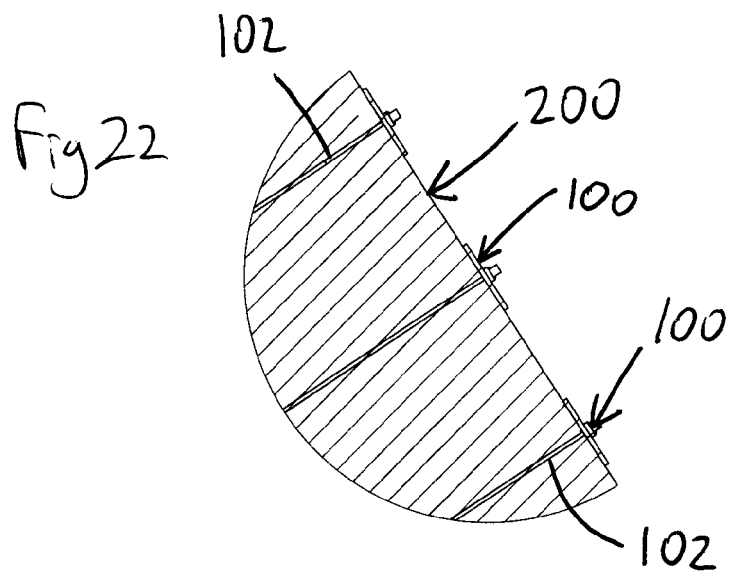
FIG. 22 is a close up view of the region marked XXII in FIG. 21.

As shown in FIGS. 18 to 22, a plurality of the securing assemblies 100 and elongate load bearing members 102 are provided to stabilise the ground forming the hill 200. As shown in FIGS. 21 and 22, the elongate load bearing members 102 extend into the hill 200, and are secured thereto by suitable means known in the art for example by the use of grouting. The elongate load bearing members 102 are tightened against the side of the hill 200 by the securing assemblies 100.

Each of the securing assemblies 100 shown in FIGS. 18 to 22 comprises a measuring arrangement 108A which can be used to measure the loads of the respective elongate load bearing members 102. This provides a determination of the stability of the ground forming the hill. The securing assemblies 100, with the elongate load bearing members 102, shown in FIGS. 18 to 22 can also be used to stabilise mine workings and tunnels.

Figure 23:
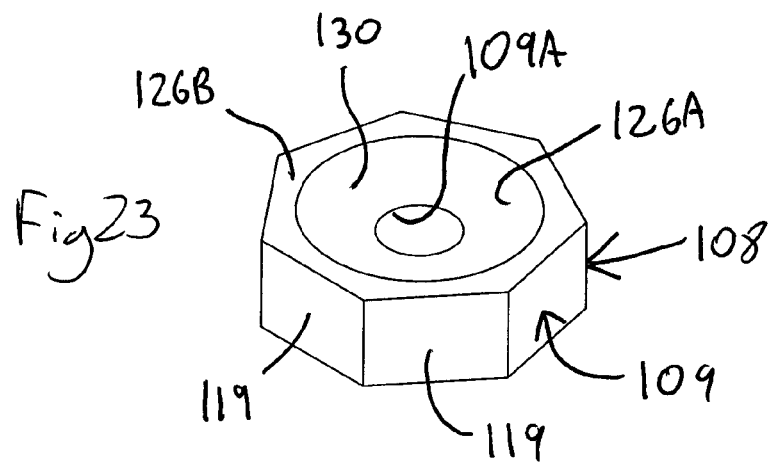
FIG. 23 is a view from below of a component of a securing assembly for use in the embodiments shown in FIGS. 9 to 22.
Figure 24:
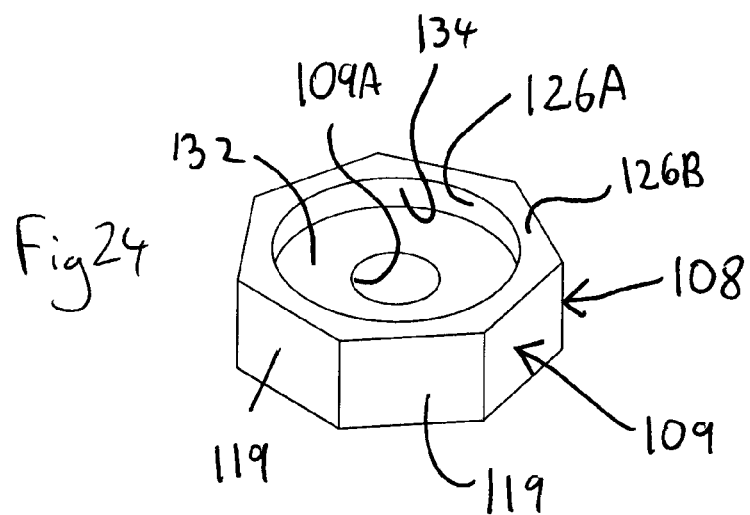
FIG. 24 is a view from below of an alternative component of the securing assembly.

FIGS. 23 and 24 show two views from below of the main bodies 109 of two measuring arrangements 108, in which the shallow recesses 126A in the main bodies 109 can be seen. In the measuring arrangement 108, the wall 130 is of a frusto-conical configuration, and slopes outwardly from the central aperture 109A to the plate engaging face 126B The recess 126A of the embodiment of the measuring arrangement 108 shown in FIG. 24 is in the form of a shallow cylinder having a first wall 132 which extends radially outwardly from the central aperture 109A, and a second wall 134 which extends from the first wall 132 to the plate engaging face 126B. The second wall 134 extends transverse to the first wall 132 and to the plate engaging face 126B.

Figure 25:
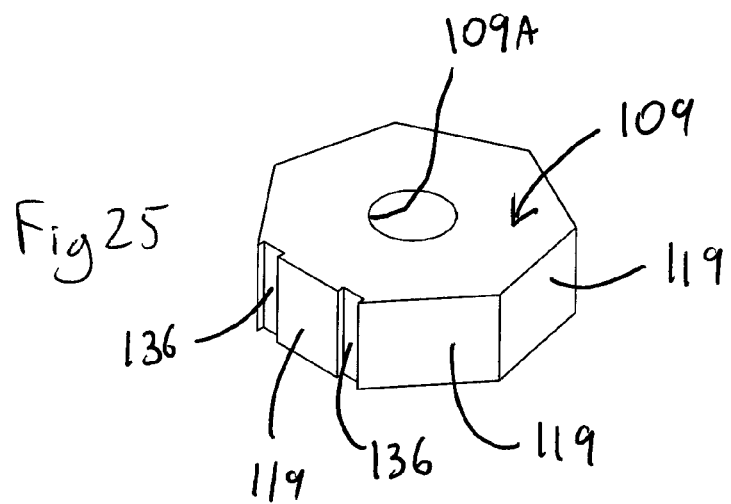
FIG. 25 is a view from above of a component of the securing assemblies shown in FIGS. 9 to 22.

FIG. 25 shows a view from above of one of the main bodies 109, showing two elongate recesses 136 in one of the edge faces 119. The ultrasonic signal emitting and receiving means 112, 114, 116, 118 are mounted in the elongate recesses 136. It will be appreciated by the persons skilled in the art that the main body 109 of the measuring arrangement 108 can be of any suitable shape. FIGS. 26A to 26F show three examples of these shapes, but it will be further appreciated that further suitable shapes can be used.

Figure 26A:
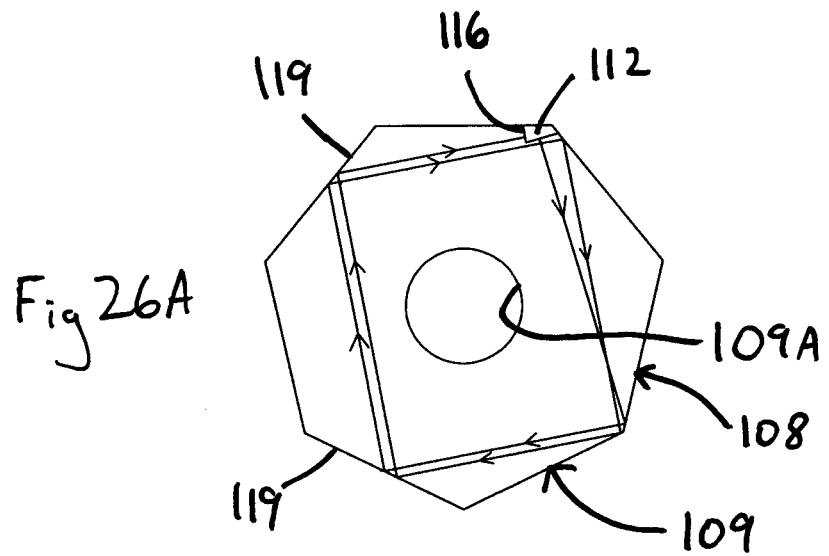
FIGS. 26A to 26F show diagrammatically the path of signals emitted through the components of the securing assembly.

In FIG. 26A, the main body 109 of the measuring arrangement 108 has a heptagonal shape, one ultrasonic signal emitting means 114, which is arranged so that the ultrasonic signal emitted thereby travels twice around the inside of the main body 109 of the measuring arrangement 108 being reflected off five of the faces 119.

Figure 26B:
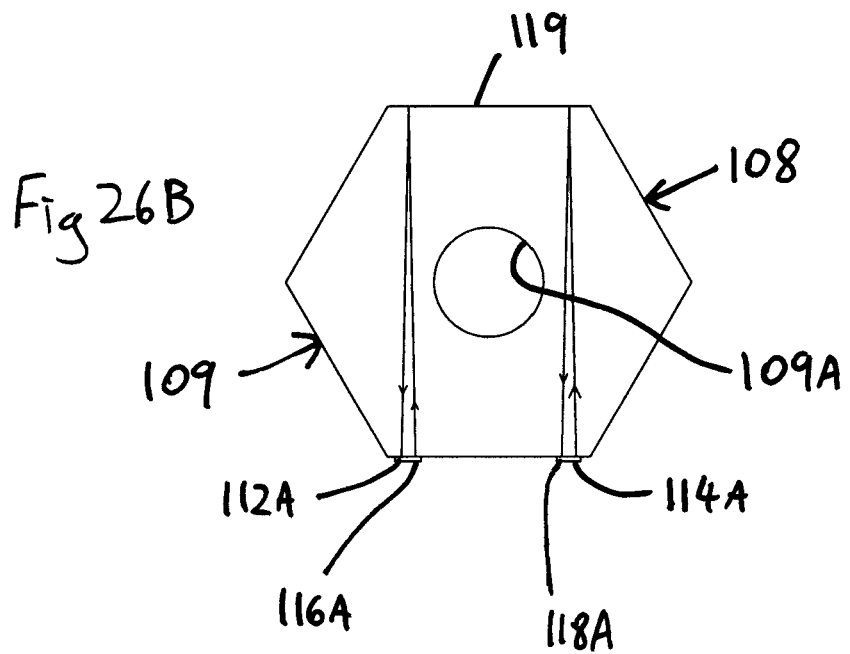

In FIG. 26B, the main body 109 of the measuring arrangement 108 is of a hexagonal configuration, and the first and second ultrasonic emitting means are in the form of two ultrasonic emitter/receivers, one of which has an ultrasonic emitter portion 112A and an ultrasonic receiver portion 116A, and the other has an ultrasonic emitter portion 114A and an ultrasonic receiver portion 118A on the same edge face 119, being configured to direct the ultrasonic signals so that they are reflected off the face 119 opposite thereto.

Figure 26C:
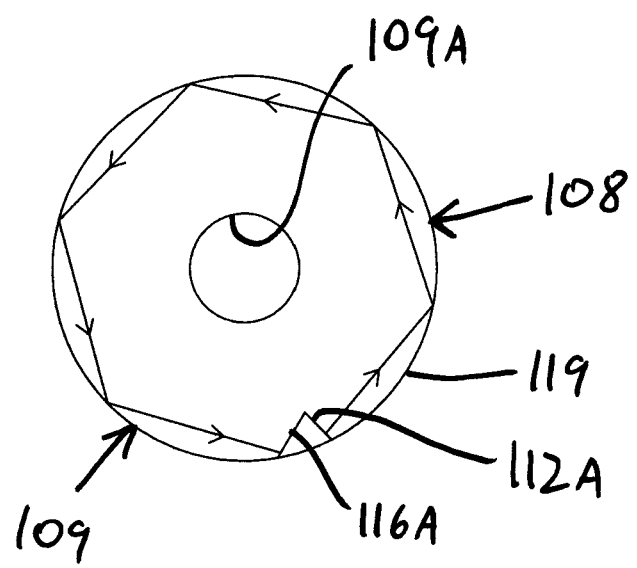

FIG. 26C shows a main body 109 of a low emitting arrangement which is of a circular shape. The ultrasonic signal emitting means is arranged to emit an ultrasonic signal to be reflected off the single circular face 119 of the main body 109 five times, before it is received by the ultrasonic signal receiving means.

Figure 26D:
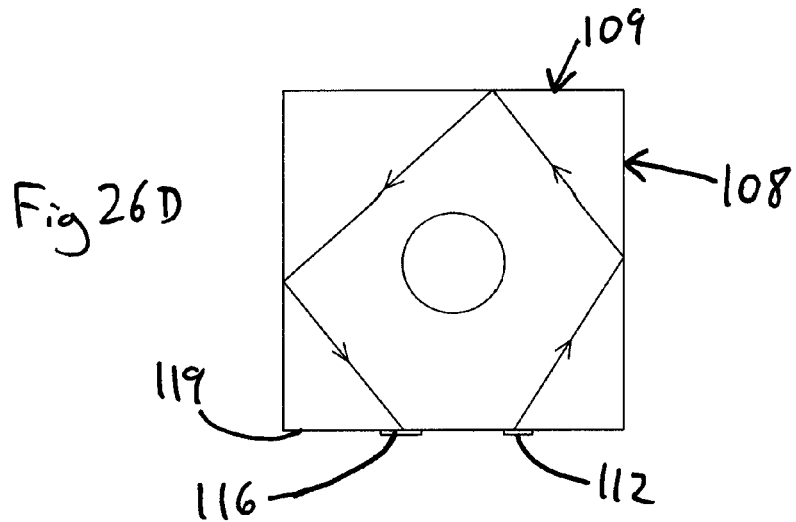
Figure 26E:
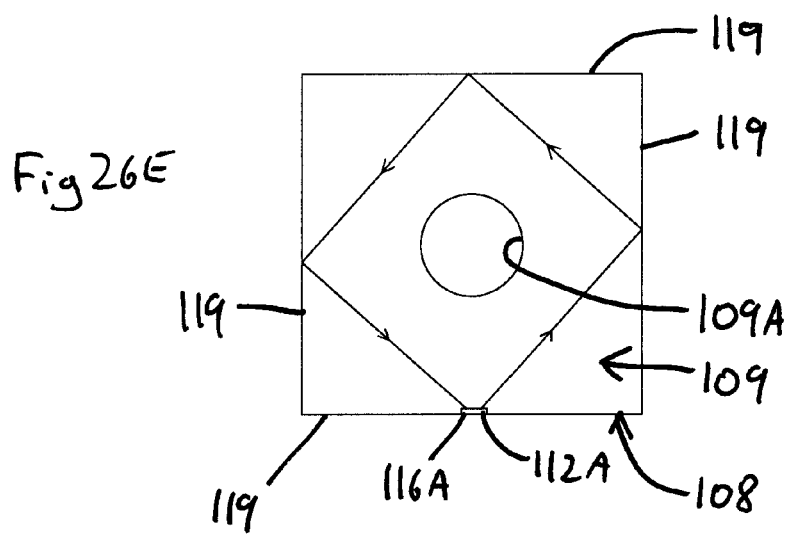
Figure 26F:
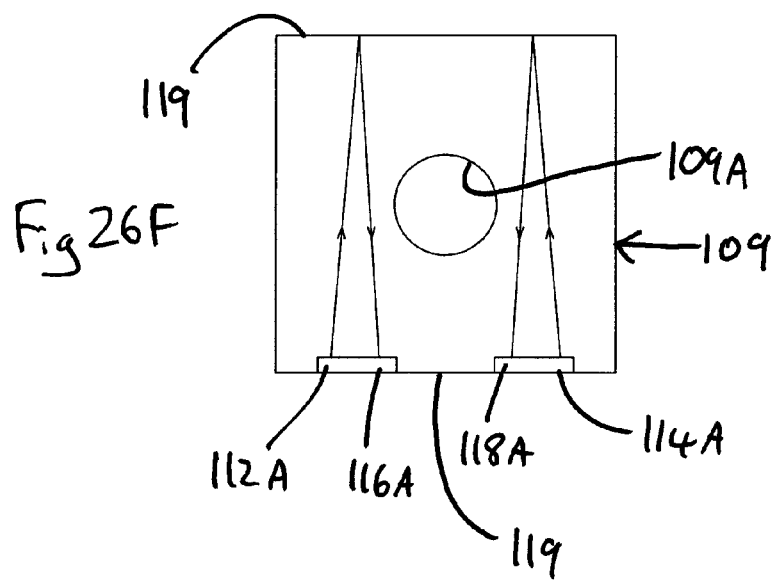

FIGS. 26D to 26F show a main body 109 of a measuring arrangement 108 which is square in shape. In FIG. 26D, the ultrasonic signal emitting means 112 is arranged to cause the ultrasonic signal to be reflected off all four faces 119 before it is received by the ultrasonic signal receiving means 116. In FIG. 26E, the ultrasonic signal emitting and receiving means is a single emitter/receiver which causes the signal also to be reflected off all four edge faces 119.

FIG. 26F shows two separate combined emitting/receiving means, the emitter portions 112A, 114A emit the ultrasonic signals so that they are reflected off the opposite edge face 119 to the receiver portions 116A, 118A. This is similar to the arrangement shown in FIG. 26B.

FIGS. 27A to 27C show the path taken by the ultrasonic signal when viewed from the side of the measuring arrangement 108. In FIG. 27A, which could be either the embodiment shown in FIG. 26B or that shown in FIG. 26F shows the signal emitted from the emitter/receiver on one face 119 to be reflected off the opposite face 119 back to the same emitter/receiver. FIGS. 27B and 27C show respectively the use of separate emitters/receivers which are arranged above and below one another. FIG. 27B shows the path of the two signals when the measuring arrangement 108 is deformed by a load L on the elongate load bearing member 102. FIG. 27C shows the same situation when no load is applied to the elongate load bearing member 102.

There are thus described, and shown in FIGS. 9 to 27C, the use of a measuring arrangement 108 to determine the load on an elongate load bearing member 102 by measurements taken transverse to the direction of the load on the elongate load bearing member 102.

The above description relates to recording measurements taken directly on the component of the securing assembly. In an alternative embodiment, the method may involve recording parameters, or derived parameters, of the measurements taken. Thus, this embodiment, the load on the load bearing member is determined using the parameters or the derived parameters.

FIGS. 28 to 31 show a crane 200 in which the pin 24A shown in FIG. 8 is used. The crane 200 comprises a support 202 and a jib 204 supported thereby. A counterweight 206 is also supported by the support to balance the jib 204.

A load bearing member, in the form of a cable 208 is provided to carry a load 210. The cable 208 is wound around a pulley 212 rotatably mounted on the jib 204 by the pin 24A, and a downwardly extending portion 208A extends from the pulley 212 to the load 210.

Figure 28:
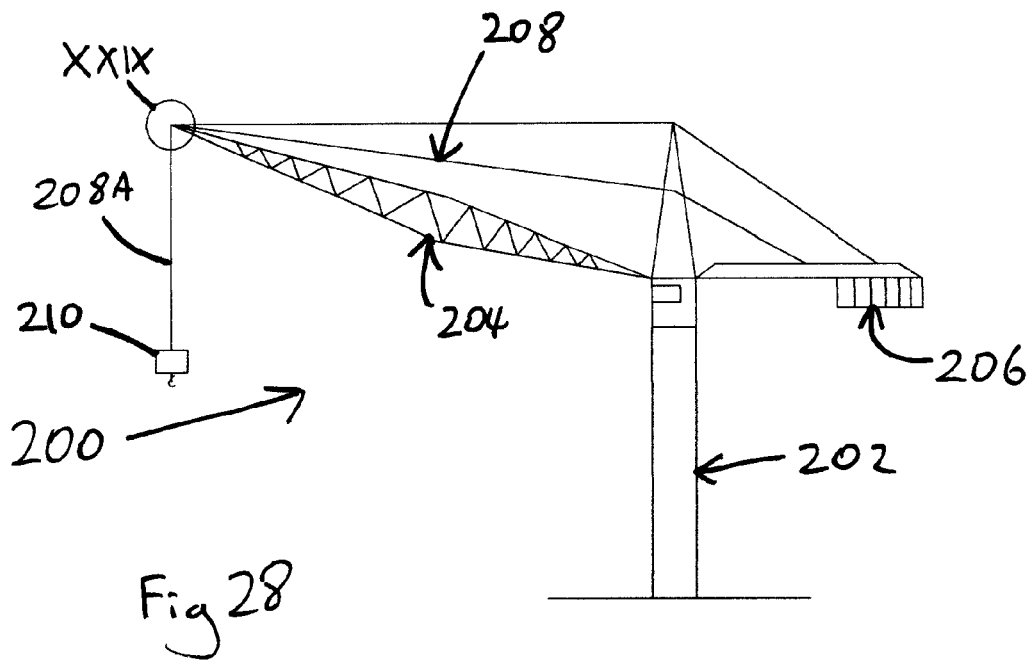
FIG. 28 shows a side view of a crane with a jib in a first position.
Figure 29:
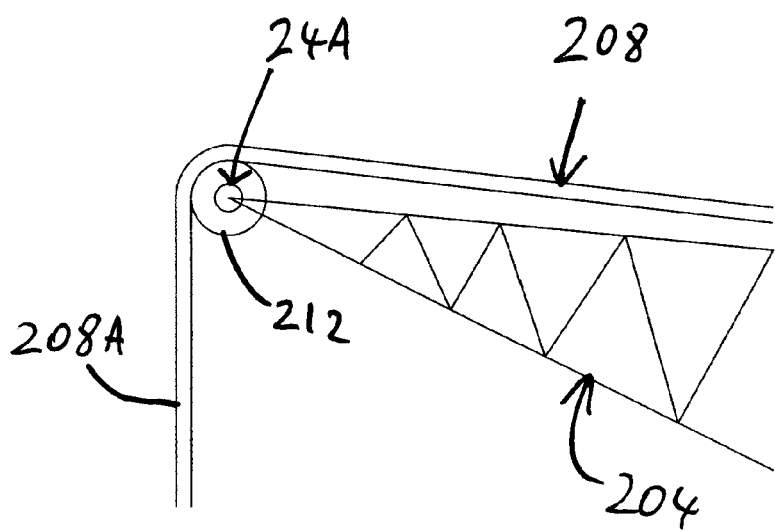
FIG. 29 is a close up of the region marked XXIX in FIG. 28.
Figure 30:
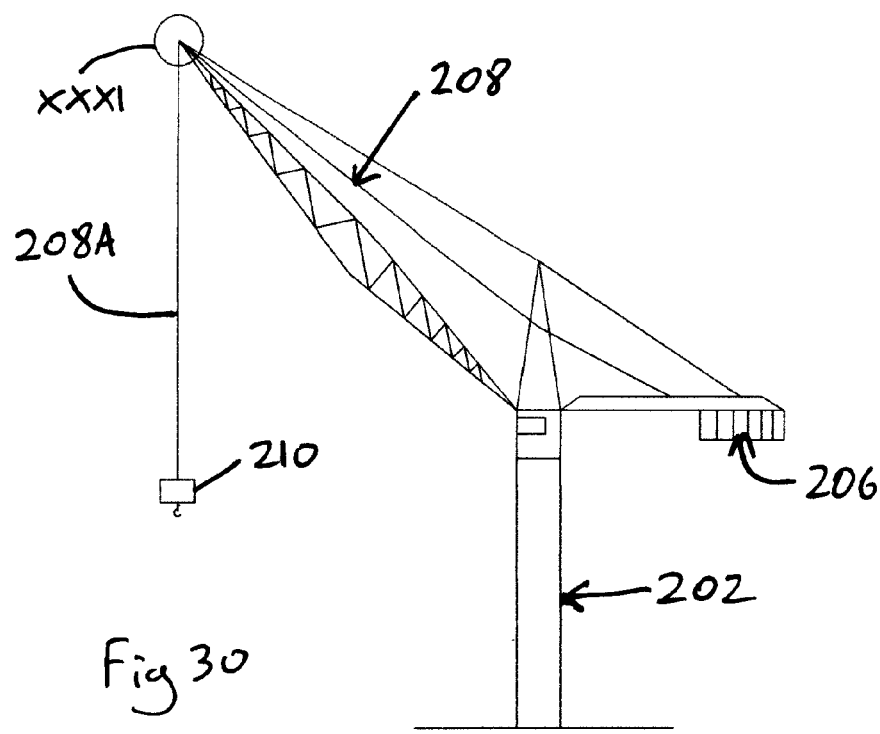
FIG. 30 shows a side view of the crane with the jib in a second position.
Figure 31:
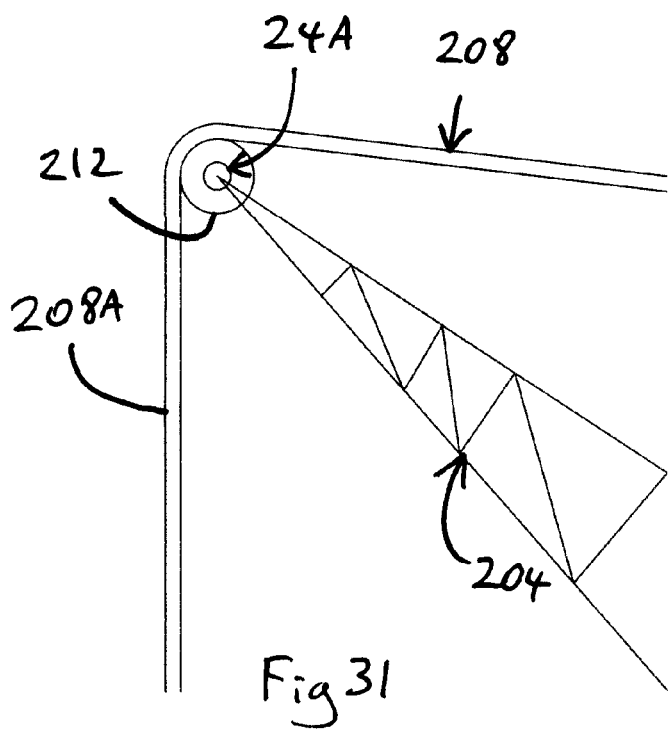
FIG. 31 is a close up of the region marked XXXI in FIG. 30.

FIGS. 28 and 29 show the crane 200 with the jib 204 in a first position, and FIGS. 30 and 31 show the jib 204 in a second position.

The pin 24A is fixedly mounted in the jib 204, Thus, as the jib 204 is moved, the pin 24A remains in a fixed position relative thereto. However, the position of the pin 24A relative to the downwardly extending portion 208A and, hence relative to the direction at which the force is applied, varies as the jib 204 moves.

However, as shown in FIG. 8 and described above, the pin 24A comprises a plurality of equally spaced emission points 32A. Thus, by taking measurements as described above at each of the emission points 32A, the load vector can be calculated giving both angle and magnitude of load, thereby allowing the load on the cable 208 to be determined, regardless of the position of the jib 204.

It will be appreciated that the pin 24A can be used in any situation where it is desirable to measure the load on a pivotable or rotatable load bearing member.

The invention claimed is:

1. A method of analysing a load bearing member in an architectural structure, the method comprising providing the load bearing member in a condition in which it is secured to a formation with a securing assembly, applying a load to the load bearing member, thereby stressing the securing assembly, transmitting first and second signals through a component of the securing assembly transverse to the direction at which the load is applied, and taking a measurement of an effect on each signal to determine the aforesaid load, wherein the first signal is transmitted through a region of the aforesaid component of the securing assembly that is in tension during said stressing of the component, and the second signal is transmitted through a region of the aforesaid component of the securing assembly that is in compression during said stressing of the component.

2. A method according to claim 1, wherein each signal is transmitted through the component of the securing assembly substantially orthogonally to the direction at which the load is applied.

3. A method according to claim 1, wherein each signal comprises a sound wave, or a plurality of sound waves, and the measurement of the effect on the signal comprises a measurement of the time for the signal to transmit through the aforesaid component of the securing assembly.

4. A method according to claim 1, wherein each signal comprises an ultrasonic wave, or a plurality of ultrasonic waves.

5. A method according to claim 1, wherein the measurement of the effect on each signal comprises a measurement of the frequency or frequency variation of the signal and/or a measurement of the amplitude or amplitude variation.

6. A method according to claim 1, wherein the aforesaid component of the securing assembly extends transverse to the load bearing member, and the stressing of the aforesaid component of the securing assembly causes the aforesaid component of the securing assembly to deform.

7. A method according to claim 1, wherein the step of transmitting the signal comprises providing two emission points on an emission face of the component securing assembly, and emitting a respective signal from each of the emission points.

8. A method according to claim 1, wherein the plurality of emission points are spaced substantially equally from a substantially central point of the emission face, and are substantially equally spaced from adjacent emission points.

9. A method according to claim 1, including emitting the signals from the emission points to the further face of the aforesaid component of the securing assembly, or to a further region of the same face of the aforesaid component of the securing assembly, to be reflected from the further face, or from the further region, to a receiving point, taking a measurement of the aforesaid effect on each signal, and recording the measurements on a recording medium.

10. A method according to claim 1, comprising transmitting a plurality of signals through the aforesaid component of the securing assembly, and taking a measurement of an effect on each signal to determine the aforesaid load.

11. A method according to claim 1, wherein the step of taking the, or each, measurement comprises emitting from a signal emission device at an emission face, a signal to be transmitted through the aforesaid component of the securing assembly transverse to the direction of the load applied to the load bearing member.

12. A method according to claim 11, wherein the signal emission device comprises a receiving device to receive a signal, and the signal is reflected from an opposite face, or an opposite region of the same face, of the aforesaid component of the securing assembly, or from a discontinuity in the aforesaid component of the securing assembly.

13. A method according to claim 11, wherein at least one receiving device to receive the, or each, signal is arranged at a region opposite the emission face, to receive the emitted signal.

14. A method according to claim 11, wherein the step of taking the, or each, measurement comprises measuring the, or each, time of flight for the, or each, signal to reach, or return to, the, or each, measurement point on the aforesaid component of the securing assembly.

15. A method according to claim 11, wherein the step of taking the, or each, measurement comprises measuring the amplitude and/or frequency variation of the signal.

16. A method according to claim 1, wherein the, or each, measurement is taken during elastic load deformation of the aforesaid component of the securing assembly.

17. A method according to claim 16, wherein the aforesaid component of the securing assembly defines a recess to facilitate, or allow the elastic deformation thereof.

18. A method according to claim 1, wherein a first signal is transmitted through a region of the aforesaid component of the securing assembly that is in tension during said stressing of the component, and a second signal is transmitted through a region of the aforesaid component of the securing assembly that is in compression during said stressing of the component.

* * * * *